United States Patent [19]
Crathern et al.

[11] Patent Number: 5,838,573
[45] Date of Patent: Nov. 17, 1998

[54] PROCESS AND APPARATUS FOR SPOTTING LABELS

[75] Inventors: Charles F. H. Crathern, Contoocook, N.H.; John DiValerio, Havertown, Pa.

[73] Assignee: Crathern & Smith, Inc., Huntingdon Valley, Pa.

[21] Appl. No.: 943,741

[22] Filed: Oct. 3, 1997

Related U.S. Application Data

[63] Continuation of Ser. No. 510,856, Aug. 3, 1995, abandoned.
[51] Int. Cl.$^6$ ..................................................... B07C 17/00
[52] U.S. Cl. .................................. 364/478.18; 364/478.01; 364/478.11; 364/470.05; 364/470.06; 364/474.08; 364/474.09
[58] Field of Search .......................... 364/478.18, 478.01, 364/478.11, 478.08, 474.09, 470.05, 470.06, 560, 506, 489, 563

[56] References Cited

U.S. PATENT DOCUMENTS

| | | | |
|---|---|---|---|
| 5,451,795 | 9/1995 | Carbrey et al. | 250/561 |
| 5,572,433 | 11/1996 | Falconer et al. | 364/471.01 |

*Primary Examiner*—Paul P. Gordon
*Assistant Examiner*—McDieunel Marc
*Attorney, Agent, or Firm*—Lappin & Kusmer LLP

[57] ABSTRACT

A system for registering containers carried on one conveyor belt with wraps carried on another conveyor belt, in which each container is viewed by an electronic camera that provides a digitized image of the container. Printed material on the face of each wrap, being carried face down on its conveyor, is viewed by another electronic camera that provides a digitized image of the printed material. The wrap conveyor comprises a flexible, light-transmissive conveyor belt supported on a light-transmissive frame. A light source is provided for lighting the wrap through the belt. In one embodiment where the wrap is light-transmissive, the printed material is viewed through the wrap itself. In another embodiment where the wrap is light-opaque, the printed material is viewed through the conveyor belt. Digitized information of standards of at least the location and details of the printed material and of the container are prestored in a computer. The latter compares the digitized images with the standards to generate commands that control a mechanical arm that correctly spots the containers on the wraps regardless of their original orientation and position.

9 Claims, 2 Drawing Sheets

PROCESS AND APPARATUS FOR SPOTTING LABELS

This application is a continuation of prior application U.S. Ser. No. 08/510,856, filed on Aug. 3, 1995 which is abandoned entitled "IMPROVED PROCESS AND APPARATUS FOR SPOTTING LABELS".

This invention relates to spotting or registration apparatus and more particularly to an automatic process of applying labels to a surface using an optical detection system to achieve proper registration.

BACKGROUND OF THE INVENTION

Spotting equipment generally can be considered to be apparatus that matches sequentially presented items to a corresponding sequence of other items in a predetermined geometrical relationship with one another, i.e. registration. For example, spotting apparatus is useful in matching labels to containers or applying flexible wrappings (i.e. wraps) to containers or boards, and the like. The terms "label" and "wrap" as used herein, sometimes interchangeably, is intended to be limited to a sheet or notice or that is inscribed or printed with information or a pattern regardless of the nature of the sheet material which may have any particularly desired flexibility, stiffness or opacity.

There are a number of prior art systems that examine objects such as containers or labels optically for a number of purposes, that can be used to automatically register labels with corresponding containers and spot the properly registered label on a surface of the container or vice-versa. Among the more advanced systems is that disclosed and claimed in U.S. patent application Ser. No. 07/234,268, now U.S. Pat. No. 5,451,795 issued Sep. 19, 1995 to Robert J. Carbrey et. al. (hereinafter the 268 application) which is incorporated herein by reference in its entirety. As pointed out in the 268 application, to effect reasonably adequate registration, for example between a wrap or label and an object such as a container, it is preferred to have detailed knowledge of the size, shape and orientation in at least two dimensions of the wrap and object. Such information with respect to the wrap and object can readily be provided by optical viewing means such as an electronic camera that views the wrap and/or object being carried on a conveyor and provides digitized images suitable for processing with any of a number of known programs in a digital computer. The 268 application shows a system comprising one or more electronic video cameras for forming respective digitized images of sequentially presented labels and sequentially presented containers as carried on respective conveyors. A digital computer is used to determine from the digitized images if the respective label and container meet predetermined quality criteria as to dimension, shape and orientation, and determines whether the label and container are matched for each other. Mechanical pick-up means are provided for physically spotting the label on the container or vice-versa in proper registration regardless of their original orientation, responsively to the computer determination. The conveyor intended to carry the labels comprises a pneumatically porous, light-transmissive conveyor belt for moving the labels on one surface thereof in sequence through the focal plane of the video camera, the belt being supported on an apertured, light transmissive frame over a vacuum plenum in which a negative pressure is maintained to releasably retain the labels on the belt. The other surface of the belt is illuminated to backlight the labels, preferably diffusely, and provide a high contrast between the belt and the label border or edges as viewed by the camera.

While the apparatus described in the 268 application has proven to be a substantial advance in the art, it is subject to a number of limitations. For example, the 268 apparatus determines the size, shape and orientation of the label by optically locating the edges or corners presented to the camera in high contrast by backlighting. If, however, the label is a clear or even a colored transparency, the camera may have great difficulty in making the necessary edge locations. While the 268 apparatus can ordinarily register the labels with the corresponding container surface with a very high degree of accuracy, if the label contains printing that is not properly registered with the label edges, then that printing will be misregistered with respect to the container outline.

A principal object of the present invention is therefore to provide a spotting system that overcomes the above-identified problems of the prior art. Yet other objects of the present invention are to provide such as system in which the signals generated by a camera viewing a conveying surface and labels supported thereon are based upon printing or other indicia appearing within the boundaries of the label carried on the conveying surface.

SUMMARY OF THE INVENTION

To effect the foregoing and other objects, the present invention generally is incorporated in apparatus for registering objects, here exemplified by containers, carried on one conveyor line with wraps carried on another conveyor line. Means are provided for determining such parameters as the shape, position, dimensions and orientation of successive containers on their conveyor line and for providing preferably digital electronic signals corresponding to such parameters. Each wrap on its conveyor line is viewed, preferably by an electronic camera that provides a digitized image of printed material on the face of the wrap, the latter being carried ordinarily face down on its conveyor so that when applied to the container the face is outward. The wrap conveyor comprises a flexible, light-transmissive conveyor belt supported on a light-transmissive frame. A light source is provided for illuminating, through the belt, the printing, design or other indicia appearing within the borders of the wrap. In one embodiment where the wrap is light-transmissive, the printed material is viewed in the illumination passing through both the belt and the wrap. In another embodiment where the wrap is light-opaque, the printed material is directly viewed on the printed surface of the wrap as illuminated through the conveyor belt. A computer determines from the digitized image of the wrap, the digital signals regarding the parameters of the corresponding container and prestored standards, sufficient information to effect registration of a container and corresponding wrap by means, such as a mechanical arm that spots the containers on the wraps regardless of their original orientation, responsively to commands from the computer.

The invention also includes a method of registering an item of a first set of thin sheet material sequentially presented on movable conveyor to a corresponding member of a sequence of another set sequentially presented on another movable conveyor, that item having a predetermined design disposed thereon within its borders. Predetermined standards, preferably in the form of digitized information of regarding, for example, the location and details of at least the design or a significant part thereof, are prestored in a computer memory. In operation of the present invention, the design on a label being carried on the conveyor is optically scanned so as to provide a digitized image thereof. Digital signals corresponding to parameters of members, such as containers, of the other set, particularly as to location and orientation, are generated by appropriate means preferably also while the members of the other set are on the corresponding conveyor. The digitized images and digital signals are then compared with the prestored standards so as to generate spotting commands; and each item and the corresponding member are physically spotted responsively to those commands in the desired registration regardless of the original orientation and position of the item and member on their respective conveyors.

BRIEF DESCRIPTION OF THE DRAWINGS

For a fuller understanding of the nature and objects of the present invention, reference should be had to the following detailed description taken in connection with the accompanying drawings in which.

DETAILED DESCRIPTION OF THE DRAWINGS

Figure 1:
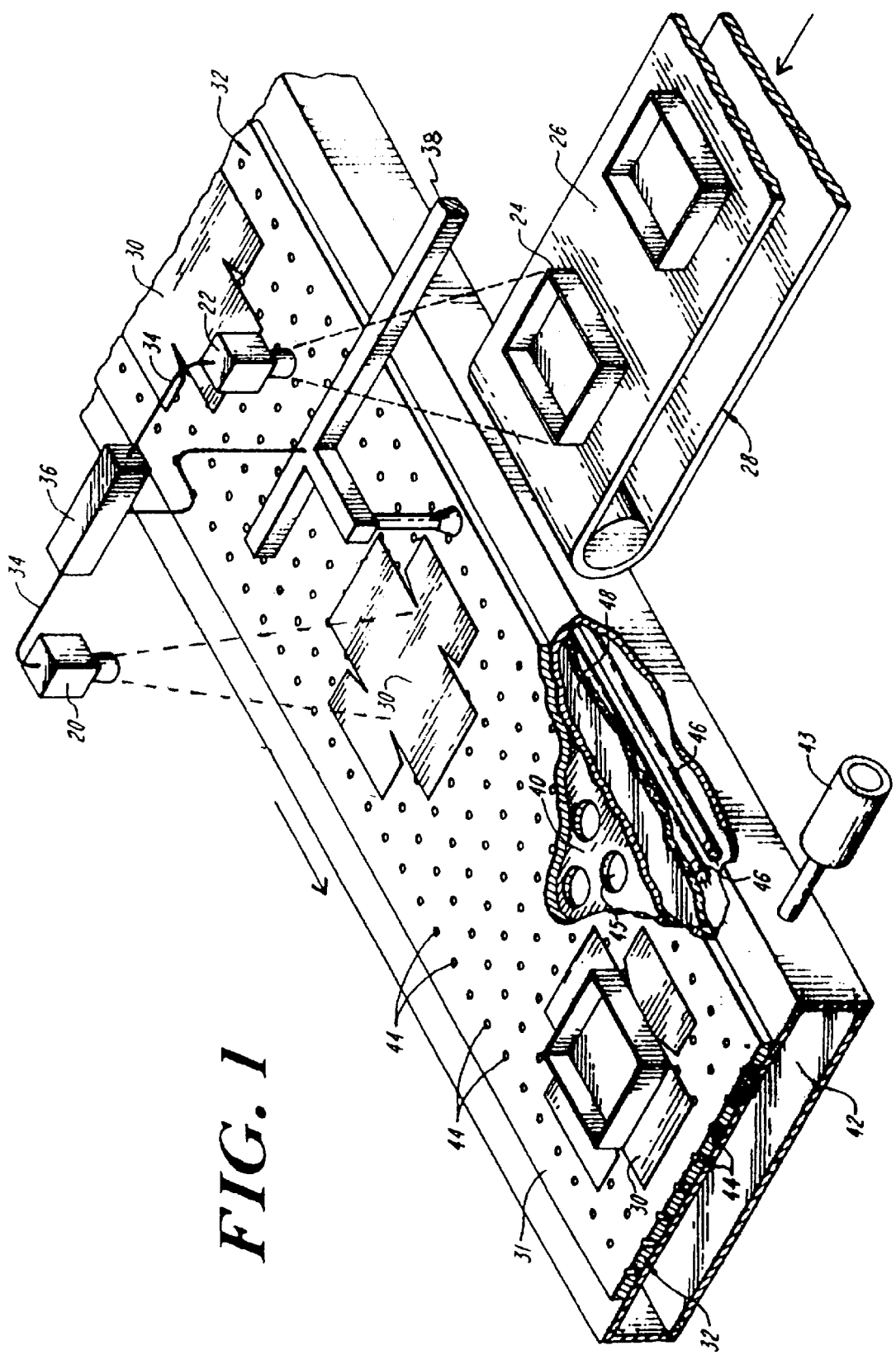
FIG. 1 is a schematic diagram, partly cut-away, illustrating a prior art embodiment of apparatus useful for effecting the method of the present invention.

The apparatus of the present invention is intended to register items of a first set of thin sheet material sequentially presented on movable conveyor means to corresponding members of a sequence of another set on another conveyor. The apparatus shown in FIG. 1 will be recognized as being substantially similar in part to that disclosed in the 268 application, and comprises video means for viewing or scanning those items and members. To this end, the apparatus of FIG. 1 includes electronic camera means typically formed of a pair of well-known charge-coupled device (CCD) video cameras 20 and 22, such as the commercially available Sony model XC-77 monochrome CCD camera. In the embodiment shown in FIG. 1, camera 22 is disposed for viewing or scanning container 24 (typically made of paper, metal, plastic and the like), preferably as a top view, against the background of a supporting surface 26 of conveyor means comprising flexible conveyor belt 28 which is intended to move a sequence of such containers. It will be appreciated that as means for determining parameters, such as location and orientation of container 24 carried on its conveyor, and providing signals corresponding to those parameters, a number of different systems, mechanical, hydraulic and the like, can be employed, but an optical system, while not mandatory, is preferred.

CCD camera 20 similarly is disposed for sequentially viewing or scanning wraps 30, typically formed of sheets of paper, plastic, and the like, as the sheets are supported on surface 31 of conveyor means comprising conveyor belt 32. The latter is intended to move a sequence of such wraps which may be randomly oriented on the belt.

In operation, CCD camera 22 provides electronic signals equivalent to images, typically digitized, of containers 24 as they are successively provided by conveyor belt 28. Such signals preferably include data as to size, shape, orientation and location of each scanned or photographed container with respect to a fixed frame of reference, either temporal or spatial, against the background of the supporting surface of the corresponding conveyor belt. In the embodiment shown in FIG. 1, each of the wraps has a predetermined design, for example printed or embossed text or other indicia including arbitrary or fanciful designs such as, but not limited to, geometric arrangements, artistic representations and the like, disposed thereon within the borders of the wrap and typically carried face-down against surface 31 of belt 32. CCD camera 20 is disposed or positioned to view that design as will be described in detail hereinafter, and to provide, in operation, electronic signals relating to the design on the corresponding wrap.

Means are provided in the form of leads 34 for feeding the image signals from the cameras to electronic computer means 36. Preferably prestored in the memory of computer means 36 is predetermined information regarding quality criteria, such as size or shape, to determine whether a container and a corresponding wrap are matched for each other. Importantly, also stored in the computer memory is additional predetermined information defining standards of at least the details, such as location, orientation, geometric aspects, and the like, of one or more exemplars of the designs printed or embossed on the wrap. Such standards can be prepared by "training" the computer by preforming an image of a printed or otherwise inscribed desired pattern or design arranged in the precise desired orientation and location and storing that information in the computer memory. Alternatively, synthetic digital models can be prepared in known manner and similarly stored in computer memory. The present invention is not limited to a single design, but instead computer means 36 can be trained to recognize and compare a plurality of patterns at various locations within the border or edges of a wrap or label. Computer means 36 is programmed to compare the images of the wrap and container with the prestored standards.

As the consequence of such comparison, computer means 36 generates a set of spotting commands to effect spotting of a container on a corresponding wrap in a location that arranges the printed material on the wrap in desired spatial relationship or registration with the container. It will be appreciated that computer means 36 can be a general purpose digital computer, a dedicated digital computer or even analog computer or hardwired circuit. Means, in the form of movable arm 38 mechanism operable responsively to the spotting commands from computer means 36 based on the information from the cameras (or location and orientation signals regarding the container and generated mechanically or otherwise as the case may be), are positioned to pick up computer-approved ones of containers 24 and spot them on corresponding computer-approved wraps 30 regardless of the original orientation of that container and wrap. The pick up of the containers by mechanism of arm 38 may be achieved by vacuum, releasable adhesion, magnetic fields or the like (depending on the nature of the container material). Typically, belt 32 is provided as a flexible mesh or pneumatically porous belt, mounted for sliding movement on the upper surface of supporting frame 40 over vacuum plenum 42 in which a negative pressure is maintained by pump 43 to releasably retain the flat wraps 30 in relatively fixed, but releasable positions on the belt. To this end, belt 32 may be provided with a plurality of apertures 44 extending between the opposed longitudinal surfaces of the belt so as to serve as pneumatically communicating passageways between the atmospheric pressure at the outer surface 31 of belt 32 and the reduced pressure in vacuum plenum 42. Similarly, frame 40 is also provided as an open network or grid, and, for example, is formed of a sheet of substantially rigid material having a plurality of large apertures or holes 45, e.g. ½" in diameter, therein through which gas can pass between plenum 42 and apertures 44. Belt 28 can be formed similarly to belt 32 but if the containers or other objects conveyed on it are relatively heavy enough to tend to remain in a fixed position (at least during viewing by camera 22 if the information regarding the containers is obtained optically), belt 28 need not be porous, and a corresponding vacuum plenum need not be provided.

Conveyor belt 32 is formed of light-transmissive (i.e. either translucent or transparent) material such as a flexible, light-transmissive urethane reinforced with light-transmissive fibers such as glass, polyester, polystyrene, polycarbonate and the like. Similarly, because belt 32 necessarily runs across frame or grid 40 which provides both support and an open structure so that the vacuum in plenum 42, if provided, may draw air through the belt, grid 40 is formed of light-transparent or highly translucent plastic or glass material, preferably of polytetrafluorethylene or other material having a very low coefficient of friction. In combination with light-transmissive belt 32 and light-transmissive supporting grid 40 is a light source, shown as a plurality of elongated electrical lamps 46, typically fluorescent, positioned within plenum 42 so as to backlight belt 32. Typically, but not necessarily, underlying frame 40 and disposed between lamps 46 and belt 32, is optical scattering or dispersive means, for example, a layer or diffuser sheet 48 of light-transmissive, frosted or opal plastic or glass.

In operation of the embodiment of FIG. 1, a model of a pattern or arrangement of text or other indicia on the label is created by training using, for example, the Cognex Searching software provided by Cognex Corporation, Needham, Mass. 02194 and as described in detail in Section 6 of Chapter 1 in *Cognex 2000/3000/4000/5000 Vision Tools*, Revision 6.0, published 1993 by Cognex Corporation. Other known software for training is available commercially from other vendors or can readily be developed in house. Training requires production of an image that contains the features of interest, and such image is preferably provided to computer 36 by imaging the desired label features with camera 20. As described in the aforesaid *Cognex 2000/3000/ 4000/5000 Vision Tools*, the image provided in digitized form is stored in the computer memory where it is transformed by the software into a model to be used in the subsequent search procedure.

Respective sequences of containers 24 and labels 30 intended to be registered with and applied to the containers are carried along respective conveyor belts 28 and 32 in the direction indicated by the arrows, to where they can be viewed by respective cameras 20 and 22. It will be appreciated that often the label is formed of paper or the like which is sufficiently light-transmissive so that opaque printing thereon can be viewed, albeit as a somewhat diffuse image, through the label as illuminated from underneath the latter. Accordingly, to effect one method of the present invention, camera 20 in the apparatus of FIG. 1, remains located as in the prior art so as to face the upper carrying surface of belt 32. Thus camera 20 will view, through a light-transmissive label, material imprinted or inscribed on that surface of the label facing belt 32.

Once the cameras have viewed a respective one of the containers and labels, the optical information regarding size, shape and orientation of the container and the printed matter on the label is digitized and fed to computer means 36 which is typically a digital computer. Inasmuch as computer means 36 has been programmed to compare the digitized images of the wrap and container with the predetermined, prestored model or standards, computer means 36, controlled by the aforementioned Cognex software or other commercially available software, generates a set of spotting commands to effect spotting of a container on a corresponding wrap in a location that arranges the printed material on the wrap in desired spatial relationship or registration with the container. Those spotting commands serve to control the timing of the servo-controlled pick-up of a container 24 by arm 38 and the motion of the arm to a precise location to spot the container in proper registration on the label. Alternatively, if the computer determines that the container and wrap are mismatched beyond preset limits, or either the container or wrap is defective in failing to meet some preestablished criteria, then the mismatched or defective items are discarded. The lighting provided by lamps 46 and the optical transmissivity of frame 40 all serve to provide a relatively high intensity, uniform light glow that is transmitted through the upper surface 31 of belt 32 and through label 30 so that the printed matter on the underside of the label can be viewed by the camera.

It will be appreciated that a light-transmissive label, if not transparent, will tend to function as a diffuser with respect to the transmission of light passing through the belt, so that the printed matter viewed through the label may not be optically sharp. If, however, the computer is programmed to view a plurality of predetermined portions, such as individual letters or design elements of the printed material at several different locations, as for example, at the approximate center of those printed letter or design elements, and the several locations are summed, then the orientation and location of the design on the label can be determined with a high degree of accuracy, notwithstanding the diffusion-induced imprecision by which the edges of the letters or design elements can be viewed.

Figure 2:
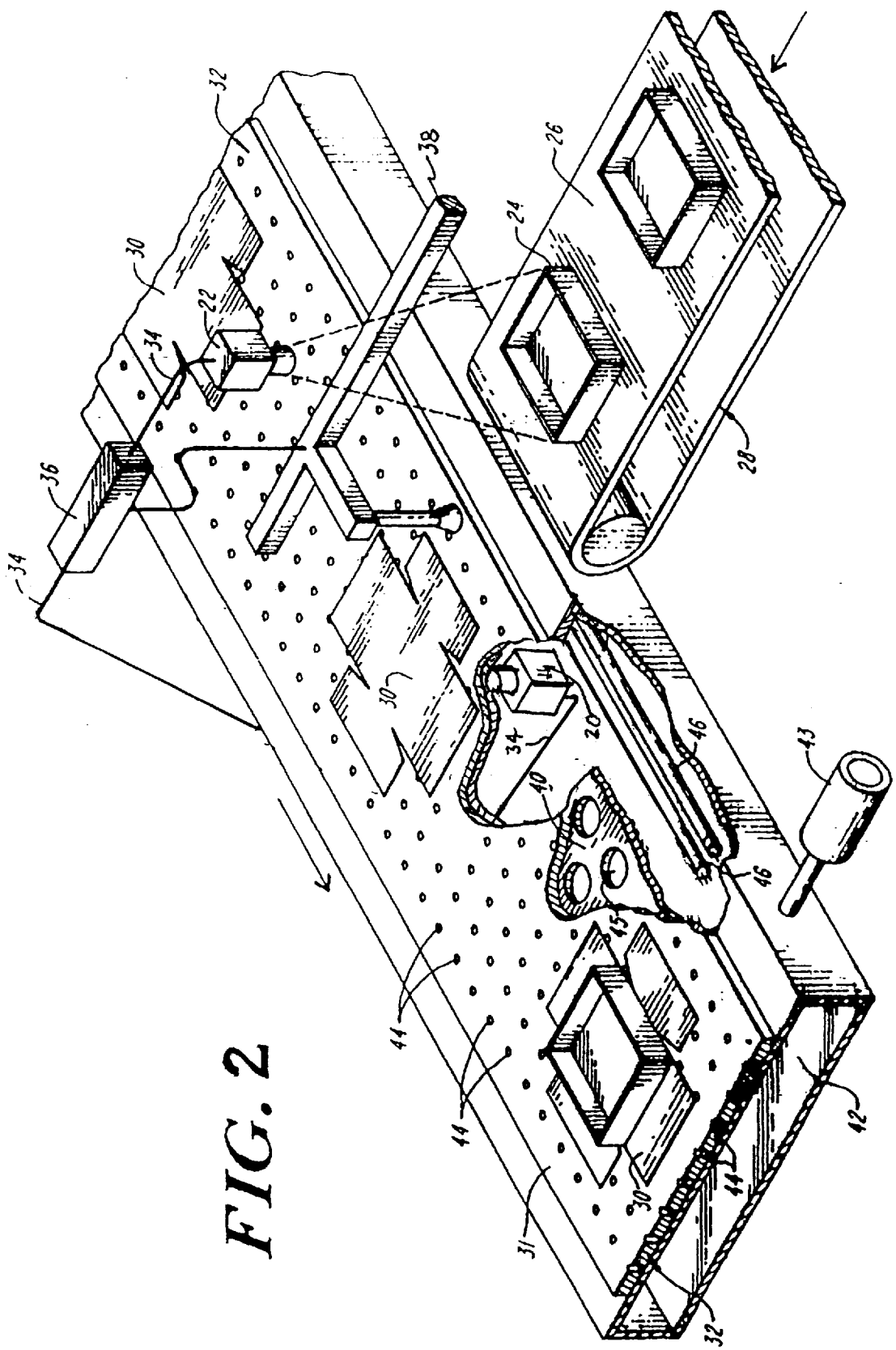
FIG. 2. is a schematic diagram, partly cut-away, illustrating a prior art embodiment of yet other and novel apparatus useful for effecting the method of the present invention.

As shown in FIG. 2, wherein like numerals denote like parts, apparatus of the present invention comprises substantially the same elements as the prior art apparatus of FIG. 1 and includes flexible conveyor belt 28 having supporting surface 26 intended to support and move a sequence of containers 24 that may be randomly oriented on the belt. The apparatus of FIG. 2 also includes a second conveyor belt 32 with an upper or outer surface 31 intended to move a sequence of labels 30 that also may be randomly oriented on belt 32. In the embodiment shown in FIG. 3, camera 22 is disposed for viewing container 24, preferably as a top view, against the background of a supporting surface 26. CCD camera 20 however, is disposed for sequentially viewing the printed surfaces of labels 30 as the latter are supported on surface 31 of belt 32, as seen through the latter, i.e. from the underside or inner surface of belt 32. Accordingly, belt 32 is formed of light-transmissive, preferably transparent, material such as a flexible, transparent urethane that may be reinforced with light-transmissive fibers such described above.

As in the embodiment of FIG. 1, the apparatus of FIG. 2 includes leads 34 for feeding the digitized image signals from the cameras to electronic computer 36. The latter is preferably programmed as described above to make the necessary comparison between the image signals and the prestored, predetermined standard in order to provide commands to effect spotting of a container on a corresponding label in a location that arranges the printed material on the label in desired registration with the container. As in the embodiment of FIG. 1, computer 36 can be a general purpose digital computer, a dedicated digital computer, an analog computer or a hardwired circuit.

Movable arm mechanism 38, operable responsively to computer commands from computer 36 based on the digitized information, as from the cameras, is positioned to pick up computer-approved ones of containers 24 and spot them on corresponding computer-approved labels 32 regardless of the original orientation of that container and label. Belt 32 may be provided as a flexible mesh or pneumatically porous belt, mounted for sliding movement on the upper surface of supporting frame 40 over a vacuum plenum 42 in which a negative pressure is maintained by pump 43 to releasably retain the flat labels 30 in relatively fixed, but releasable positions on the belt. Accordingly, belt 32 may be pneumatically porous. As in the embodiment of FIG. 1, frame 40 is typically an open grid formed of a substantially rigid material having a plurality of large apertures or holes 45 and is light-transparent. One or more electrical lamps 46 are positioned so as to backlight belt 32. In order to preserve the optical clarity of images of printed matter on the labels as viewed through belt 32, the embodiment of FIG. 2 has dispensed with any optical scattering means or diffuser between the belt and lamps 46.

The advantages of the embodiment of FIG. 2 are immediately apparent in that the labels can be formed of any material, light-opaque or light-transmissive and thus will accept, for example metallic foil labels, unlike the system above described in which the printed matter on the labels is read through the label. Additionally, the images provided of the printed matter on the labels tend to be optically much sharper than those read through the label, so less computer processing may be required. Additionally, the light flux required to read the printed matter directly from the face of the label can be relatively low and expected to be considerably less than that required to read the printed matter through the label or to provide the high contrast between background and edges desired by the system of the '667 application. Hence, the illumination requirements for the apparatus of FIG. 2, need be considerably less and thus generate less heat and use less power.

Since certain changes may be made in the above apparatus without departing from the scope of the invention herein involved, it is intended that all matter contained in the above description or shown in the accompanying drawings shall be interpreted in an illustrative and not in a limiting sense.

What is claimed is:

1. In apparatus for physically registering separate, individual items of thin sheet material of a first set sequentially presented on a movable conveyor belt to corresponding individual members of a sequence of a second set, said apparatus including means for releasably retaining said items on a surface of said conveyor belt, video means for viewing said items on said surface of said conveyor belt and for providing first signals representative of said viewing, means for establishing parameters of said members of said second set and for providing second signals representative of said parameters, computer means for determination of sufficient information from said signals to provide commands to effect such registration, means for physically spotting at least one of said items with respect to one of said members in said registration regardless of the original orientation of said items and members and responsively to commands from said computer means, each of said items having at least one predetermined design disposed thereon within the borders of said item, said conveyor means being a flexible, light-transmissive conveyor belt for supporting and moving said items with said design face down against an upper surface of said belt, and means for illuminating the opposite surface of said belt so as to provide illumination of said items of said first set on said one surface of said belt, the improvement wherein said video means is disposed for sequentially viewing each said design on a corresponding one of said items on said belt, as each said design is illuminated by transmission of said illumination through both said belt and said corresponding one of said items, so as to provide first signals as representative of each said design;

means for forming first digitized information from said first signals;

means for storing second digitized information of at least the location and details of a standard of said design; and means for comparing said first digitized information with said standard and for comparing said first digitized information with said second digitized information so as to determine said commands.

2. Apparatus for registration of items as set forth in claim 1, wherein said predetermined design is inscribed text.

3. Apparatus for registration of items as set forth in claim 1, wherein said predetermined design is arbitrary or fanciful.

4. Apparatus for registration of items as set forth in claim 1, wherein said means for comparing comprises computer means.

5. Apparatus for registration of items as set forth in claim 4, wherein said means for storing comprise a memory of said computer means.

6. Apparatus for registration of items as set forth in claim 4, wherein said computer means is a digital computer.

7. Method of registering an item of a first set of thin sheet material sequentially presented on movable conveyor to a corresponding member of a sequence of another set sequentially presented on another movable conveyor, said item having a predetermined design disposed thereon within the borders of said item, storing information of standards of at least the location and details of said design;

optically scanning said item on the corresponding conveyor so as to provide first signals representative of said viewing, providing second signals representative of parameters of said members of said second set;

comparing information from said first signals with said second signals so as to determine spotting commands; and physically spotting said item with respect to said member in said registration regardless of the original orientation and position of said item and member and responsively to said commands.

8. Method for registration of items and members as set forth in claim 7 wherein said step of providing said first signals includes the step of first comparing said first digitized signals with said standard to generate said information.

9. Method for registration of items and members as set forth in claim 8 including the step of digitizing said standards and signals so that they can be stored and compared in digital form.

* * * * *